United States Patent [19]

Rohrbach et al.

[11] 4,381,345

[45] Apr. 26, 1983

[54] PRETREATMENT OF GLUCOSE FEEDSTOCK WITH REDUCING AGENTS

[75] Inventors: Ronald P. Rohrbach, Forest Lake; Mary J. Maliarik, Lake Forest, both of Ill.

[73] Assignee: UOP Inc., Des Plaines, Ill.

[21] Appl. No.: 261,996

[22] Filed: May 8, 1981

[51] Int. Cl.$^3$ .......................... C12P 7/00; C12P 19/24
[52] U.S. Cl. ...................... 435/94; 435/174; 426/48; 127/46.1; 127/30
[58] Field of Search ................ 435/94, 184, 234, 161, 435/162, 188, 105, 174; 426/48; 127/52, 46.1, 50, 51, 30, 37

[56] References Cited

U.S. PATENT DOCUMENTS 3,627,636 12/1971 Jaffe et al. ................... 127/37 X
4,009,075 2/1977 Hoge ........................... 435/162
4,288,548 9/1981 Barrett et al. .................. 435/94
4,310,628 1/1982 Leiser ........................... 435/94

OTHER PUBLICATIONS

Wen-Pin Chen, Glucose Isomerase (A Review), Process Biochemistry, Aug./Sep. 1980, p. 36.
Chem Abstracts, vol. 60:14860 c-h, 1964.

*Primary Examiner*—Kenneth M. Schor
*Attorney, Agent, or Firm*—James R. Hoatson, Jr.; Eugene I. Snyder; William H. Page, II

[57] ABSTRACT

Commercial glucose solutions used as feedstocks for enzymatic conversion of glucose to fructose by glucose isomerase often contain materials which act as poisons toward the enzyme. It has been found that these poisons can be removed, or destroyed, by treatment of the feedstock with reducing agents which are water soluble and water stable metal hydrides, such as sodium borohydride.

8 Claims, No Drawings

PRETREATMENT OF GLUCOSE FEEDSTOCK WITH REDUCING AGENTS

BACKGROUND OF THE INVENTION

Fructose, or grape sugar, has been used as a sugar substitute in many applications. Increasing sugar prices spur increased fructose usage, and current fructose production is at an all-time peak.

The largest commercial source of fructose is glucose, an end product of starch hydrolysis, which is isomerized to fructose by enzymatic methods using glucose isomerase. Because the high enzyme cost dictates its reuse, the isomerization is not done homogeneously where recovery of enzyme would be difficult and costly, but instead is performed heterogeneously using glucose isomerase immobilized in some manner. That is, either cells containing glucose isomerase, or the enzyme itself, is physically and/or chemically bound to a support through which flows a glucose feedstock, with isomerization of glucose to fructose attending contact of the feedstock with the immobilized glucose isomerase system (IMGI).

It is highly desirable to have the IMGI as productive as possible. A measure of its productivity is its half-life, by which is meant the time necessary to reduce the activity of an IMGI to one-half its initial value. We have repeatedly observed that the half-life of an IMGI was longer using a purified glucose feedstock than with a commercial feedstock. These observations led to the discovery that the deleterious effect on IMGI half-life was directly associated with the presence of carbonyl-containing components in the feedstock which formed a precipitate with 2,4-dinitrophenylhydrazine. It was further discovered that removal of these components, or poisons, from the feedstock led to a substantial increase in the half-life, and thus the productivity, of IMGI. A crucial discovery leading to the invention described herein is that certain reducing agents very effectively chemically alter these poisons, or deleterious components, in a glucose feedstock, thereby rendering them innocuous and, in effect, removing the poisons initially present.

SUMMARY OF THE INVENTION

An object of this invention is to increase the productivity of immobilized glucose isomerase systems. An embodiment comprises treating a glucose feedstock with a reducing agent at a pH from about 7 to 9. In a more specific embodiment the reducing agent is sodium borohydride. In a still more specific embodiment the reducing agent is sodium borohydride used at a pH from about 8 to about 9.

DESCRIPTION OF THE INVENTION

The invention claimed herein is a process of treating a glucose feedstock prior to enzymatic conversion to fructose comprising contacting the feedstock with an effective amount of a reducing agent at a pH from about 7 to about 9 at a temperature from about 10° to about 80° C. It has been found that such treatment substantially increases the productivity of the enzyme glucose isomerase when used in an immobilized enzyme system, such increasing productivity being manifested by an increased half-life of the IMGI.

The problem which this invention solves is that commercial glucose feedstocks for fructose formation via IMGI frequently contain poisons which substantially reduce the productivity of IMGI as manifested by its half-life. For example, if an IMGI has a half-life of 70 to 80 days with a purified glucose feedstock, the IMGI may have a half-life of only from about 25 to 40 days with a commercial glucose feedstock. For the purpose of this application, the term "poisons" refers to materials found in commercial glucose feedstocks which contribute to a decrease in half-life of the immobilized glucose isomerase.

A characteristic common to glucose feedstocks exhibiting a deleterious effect on the half-life is the presence of components in minor amounts which form precipitates with 2,4-dinitrophenylhydrazine. Although the nature of these minor components is not known with certainty, it was possible to qualitatively correlate their amount, via their derivatives with 2,4-dinitrophenylhydrazine, with the extent of the reduction in half-life of IMGI. Thus, the greater the amount in the feedstock of components which form derivatives with 2,4-dinitrophenylhydrazine, the less the half-life of the IMGI. It also was observed that when the feedstock in which such components were initially absent was treated so as to induce formation of these components, the resulting feedstock substantially reduced the half-life of IMGI.

An inference which may be drawn from these observations is that the minor components forming precipitates with 2,4-dinitrophenylhydrazine are themselves poisons, or that the presence of the poisons is associated with the presence of the minor components. Although it is unknown which inference is the more correct one, this invention may be successfully practiced nonetheless. Similarly, although at least one of the minor components may be a 3-deoxyhexosone it is not known unequivocally that this is present when precipitates form with 2,4-dinitrophenylhydrazine, nor is its effect as a poison independently known.

It was subsequently discovered that treating the feedstock containing the poisons with certain reducing agents destroy the forementioned minor components, with the treated feedstock showing no deleterious effect on enzyme productivity. This discovery led to the process of this invention, which is essentially a method of removing certain minor components having a deleterious effect on the productivity of the IMGI from a glucose feedstock.

The process of this invention comprises contacting a feedstock with an effective amount of a reducing agent. The reducing agents which may be used in the process of this invention are water soluble and water stable metal hydrides. Chief among these is sodium borohydride and related compounds where from 1 to 3 of the hydrogens are replaced by other moieties, such as cyano and alkoxy containing up to about 5 carbon atoms. Examples of substituted borohydrides, all of which are sodium salts, include cyanoborohydride, dicyanoborohydride, methoxyborohydride, dimethoxyborohydride, trimethoxyborohydride, ethoxyborohydride, diethoxyborohydride, triethoxyborohydride, propoxyborohydride, dipropoxyborohydride, tripropoxyborohydride, butoxyborohydride, dibutoxyborohydride, tributoxyborohydride, and so forth. Examples of other water soluble and water stable metal hydrides include potassium borohydride, aluminum borohydride, and beryllium borohydride.

The amount of reducing agent effective in the practice of this invention depends somewhat on the agent, the amount of poison present in the feed, and the pH at which treatment is performed. Generally, the reducing agent of this invention will be effective in amounts from about 20 to about 500 ppm. In particular, when sodium borohydride is used at a pH from about 8 to about 9, an amount from about 40 to about 200 ppm constitutes an effective amount, and an amount from about 50 to about 150 ppm is even more desirable. As the pH decreases, the amount necessary to be effective in the practice of this invention increases.

As previously stated, the process of this invention is pH dependent. At a pH less than about 7, the reducing agents of this invention become unstable and decompose. On the other hand, it is found that at a pH greater than about 9 there are formed color bodies which are undesirable from a commercial aspect. Thus, a pH range from about 7 to about 9 is desirable in the practice of this invention, and the range from about 8 to about 9 is preferred.

The contact time is dependent upon the temperature, pH, the amount of oxidizing agent used, and the amount of undesirable components present. A temperature from about 10° to about 80° C. may be employed, with contact time decreasing with increasing temperature. At a pH of about 9 with about 100 ppm sodium borohydride, a contact time of about 30 minutes at about 20° C., is adequate to maximize the beneficial effects of the process of this invention. It is to be understood that at a different pH and/or using a different reducing agent, the necessary contact time may differ from that stated above, but can be readily determined through simple experimentation.

The examples below are merely illustrative of this invention which is not to be limited thereto.

EXAMPLE I

In all the examples IMGI was a preparation where glucose isomerase was immobilized unto a support matrix comprised of alumina impregnated with polyethylenimine subsequently cross-linked with excess glutaraldehyde so as to furnish excess pendant aldehyde groups. Reactors were of the fixed bed type operated at 60° C. with feedstock in an upflow mode and a space velocity sufficient to afford 42% fructose in the effluent.

In this example two reactors were run in series. The feedstock was 45% weight/weight purified glucose (Cerelose TM) containing 0.1% sodium sulfite and 7 ppm sodium omadine at pH 8.0. The feedstock gave no precipitate when treated with 2,4-dinitrophenylhydrazine. It had been found by independent experimentation that passage of the purified feedstock through IMGI caused formation of undesirable minor components. In this example the normal mode of operation consisted of passing the feedstock through the first reactor, then using the effluent from the first reactor as the feedstock for the second reactor. In this mode the second reactor performed only a small chemical change, to 48% fructose, since the feedstock at 42% fructose already was near equilibrium for the liquid hourly space velocity used. However, the second reactor was exposed to poisons formed in the first reactor. Periodically, the second reactor was fed with the purified glucose feedstock and its activity measured. This was done solely in order to determine its half-life. It was found that the half-life of the first reactor was about 144 days, whereas the half-life of the second reactor was about 84 days.

This experiment isolates and demonstrates the effect of poisons in the feedstock on the half-life of IMGI.

EXAMPLE II

Commercial feedstock containing operationally appreciable amounts of poisons, as determined by formation of 2,4-dinitrophenylhydrazine derivatives, was treated with varying amounts of sodium borohydride at pH 9 for 30 minutes at room temperature. When the borohydride was used at a concentration greater than about 100 pm no observable precipitate formed. When the borohydride was used at 40 ppm an observable but slight precipitate formed. When borohydride was absent a fairly heavy precipitate formed. Thus, poisons were present at a level requiring at least 40 to about 100 ppm of reducing agent in this particular feedstock.

EXAMPLE III

A portion of a commercial feedstock was treated for 30 minutes at ambient temperature and pH 9.0 with 100 ppm sodium borohydride. To this feedstock was added 1000 ppm sodium sulfite and the pH was adjusted to 8.2. No precipitate was formed upon addition of 2,4-dinitrophenylhydrazine. Another portion of the feedstock was treated identically except sodium borohydride was omitted. The two feedstocks were used in two reactors operating in tandem to determine half-life of the IMGI. Results are given below.

|  | Sodium Borohydride Treated Feed | Untreated Feed |
| --- | --- | --- |
| Initial Activity (units per gram) | 1820 | 1440 |
| Half-Life (days) | 63 | 36 |

Thus, sodium borohydride treatment increases the half-life of IMGI by 75% relative to untreated material.

What is claimed is:

1. In a method of converting glucose to fructose using an immobilized glucose isomerase system, the improvement wherein a feedstock containing glucose and minor amounts of isomerase poisons, prior to contacting with the immobilized glucose isomerase system, is treated with a water soluble and water stable metal hydride at a pH from about 7 to about 9 at a temperature from about 10° to about 80° C. for a time and in an amount effective to increase the productivity of said immobilized glucose isomerase system above that productivity occurring when the enzymatic isomerization is carried out without the presence of said metal hydride, the treatment being for a time sufficient to destroy said poisons.

2. The process of claim 1 wherein the hydride is selected from the group consisting of sodium borohydride, and cyano and alkoxy-substituted sodium borohydrides.

3. The process of claim 2 where the hydride is sodium borohydride.

4. The process of claim 2 where the hydride is sodium cyanoborohydride.

5. The process of claim 1 where the pH is between about 8 and about 9.

6. The process of claim 1 where the effective amount is between about 20 and about 500 parts per million.

7. The process of claim 6 where the amount is between 40 and about 200 parts per million.

8. The process of claim 7 where the amount is from about 50 to about 150 parts per million.

* * * * *